United States Patent [19]
Muller et al.

[11] Patent Number: 5,464,761
[45] Date of Patent: Nov. 7, 1995

[54] PROCESS FOR THE ENZYMATIC PREPARATION OF ALIPHATIC ALCOHOLS AND ALDEHYDES FROM LINOLEIC ACID, LINOLEIC ACID, OR A NATURAL PRECURSOR

[75] Inventors: Bernard Muller, Chambesy, Switzerland; Antoine Gautier, Lawrenceville, N.J.; Christopher Dean, Grand-Lancy; Jean-Charles Kuhn, Geneva, both of Switzerland

[73] Assignee: Firmenich S.A., Geneva, Switzerland

[21] Appl. No.: 185,786

[22] PCT Filed: May 3, 1993

[86] PCT No.: PCT/EP93/01057

§ 371 Date: Jan. 21, 1994

§ 102(e) Date: Jan. 21, 1994

[87] PCT Pub. No.: WO93/24644

PCT Pub. Date: Dec. 9, 1993

[30] Foreign Application Priority Data

May 26, 1992 [CH] Switzerland ............................. 1693/92
Jul. 28, 1992 [CH] Switzerland ............................. 2372/92
Oct. 1, 1992 [CH] Switzerland ............................. 3075/92

[51] Int. Cl.$^6$ ................................. C12P 7/24; C12P 7/64; C12P 7/02; C12P 1/02
[52] U.S. Cl. ......................... 435/147; 435/134; 435/155; 435/171
[58] Field of Search ...................................... 435/132, 134, 435/136, 147, 155, 156, 157, 171

[56] References Cited

U.S. PATENT DOCUMENTS 4,769,243  9/1988  Kanisawa et al. ........................ 426/33
4,806,379  2/1989  Goers et al. ........................... 426/650

FOREIGN PATENT DOCUMENTS 8912901  4/1991  France.

OTHER PUBLICATIONS

Luckner, In: "Secondary Metabolism Microorganisms, Plants, and Animals", Publisher: Springer–Verlag pp. 146–147, 1990.

Piazza, G. J., "Lipoxygan Lipoxygenase Cataling & Hydroperoxide Formation in Microemulsion Containing Nonionic Surfactant," *Biotechnol Letters*, vol. 14, No. 12, pp. 1153–1158 1992.

Zhang, P. et al., "Enzymatic Asymmetric Hydrozation of Pentadiamo Using System Liporganic", *J. Am Chem Soc.*, vol. 111, pp. 9241–9242 1989.

"Chemistry and Physics of Lipids, vol. 44, Nos. 2–4, Jul.–Sep. 1987, 341–361, :Biosynthetic pathway for C6–Aldehydes Formation From Linolenic Acid in Green Leaves", Akikazu Hatanaka et al.

Agric. Biol. Chem., 43(5), 969–980, 1979, "Volatile C6–Aldehyde Formation via Hydroperoxides from C18–Unsaturated Fatty Acids in Etiolated Alfalfa and Cucumber Seedlings", Jiro Sekiya, et al.

Chemical Abstracts, vol. 111, 1989, Columbus, Ohi, abstract No. 74853n, Hatakaka, Akikazu et al., "Biogeneration of green odor (I). Enzymic oxygen–active–cleavage reaction of linolenic acid in leaves", p. 455; column L.

*Primary Examiner*—David M. Naff
*Attorney, Agent, or Firm*—Pennie & Edmonds

[57] ABSTRACT

The aldehydes, N-hexanal, 3-(Z)-hexen-1-al and 2-(E)-hexen-1-al, and their corresponding alcohols are enzymatically produced in high yield from linoleic, linolenic acid or a natural precursor thereof such as hydrolyzed oil. The acid or natural precursor is mixed with soy flour containing lipoxygenase which converts the acid to 13-hydroperoxy-octadeca-9,11-dienoic acid or 13-hydroperoxy-octadeca-9,11,15-trienoic acid. Guava homogenate containing lyase is added to convert the 13-hydroperoxy-octadeca-9,11-dienoic acid into n-hexanal or the 13-hydroperoxy-octadeca-9,11,15-trienoic acid into 3-(Z)-hexen-1-al. The n-hexanal or 3-(Z)-hexen-1-al is recovered, or reduced with yeast to n-hexanol or 3-(Z)-hexen-1-ol, respectively. Alternatively, the 3-(Z)-hexen-1-al is isomerized to obtain 2-(E)-hexen-1-al which is recovered or reduced with yeast to 2-(E)-hexen-1-ol which is recovered. The yeast used for reducing and isomerizing is *Saccharomyces cerevisiae*. Steam distillation and/or extraction with an inert organic solvent is used in recovery of the aldehydes and alcohols.

15 Claims, 3 Drawing Sheets

PROCESS FOR THE ENZYMATIC PREPARATION OF ALIPHATIC ALCOHOLS AND ALDEHYDES FROM LINOLEIC ACID, LINOLEIC ACID, OR A NATURAL PRECURSOR

TECHNICAL FIELD

The present invention relates to the field of organic synthesis, more particularly, it provides an enzymatic process allowing the preparation of aldehydes and alcohols having six carbon atoms, namely n-hexanal, 3-(Z)-hexen-1-al, 2-(E)-hexen-1-al and their corresponding alcohols. These are oxygen-containing compounds of current use in the flavor industry, namely as a result of their fruity and green type organoleptic characters. There are many studies described in the literature related to a variety of synthetic methods for preparing these compounds, which are known to be constituents of several flavors of natural origin.

Given the legal prescriptions presently in force in most countries with regard to the use of food additives, it becomes imperative to have at one's disposal the above-mentioned alcohols and aldehydes in a quality capable of fulfilling the established criteria as regards their natural origin character.

Although, in principle, one could imagine obtaining these compounds via extraction of the natural origin products which contain them, it is quite obvious that, given their proportions, such a method is hardly economical.

PRIOR ART

Amongst the studies described in the literature relating to methods for synthesizing the above-mentioned compounds, one should cite that described in French patent application no. 2652587, published on Apr. 5, 1991, which relates to a biological process for the preparation of 3-(Z)-hexen-1-ol, starting from unsaturated fatty acid. The described process resorts to the combined action of a natural enzymatic system, put in under the form of radish or Rumex stalks, and of a yeast capable of promoting the reduction of 3-(Z)-hexen-1-al into 3-(Z)-hexen-1-ol. According to the authors, such a process made it possible to improve the yields in desired alcohol relative to the results obtained with previously used biological processes, such as for example those described in U.S. Pat. Nos. 4,769,243 or 4,806,379.

Although we have been able to ascertain the validity of this claim, parallel studies carried out by us have shown that it was possible to go substantially beyond the efficiency coefficients indicated in the cited patent application, thanks to the process which is the object of the present invention.

DESCRIPTION OF THE INVENTION

Figure 1:
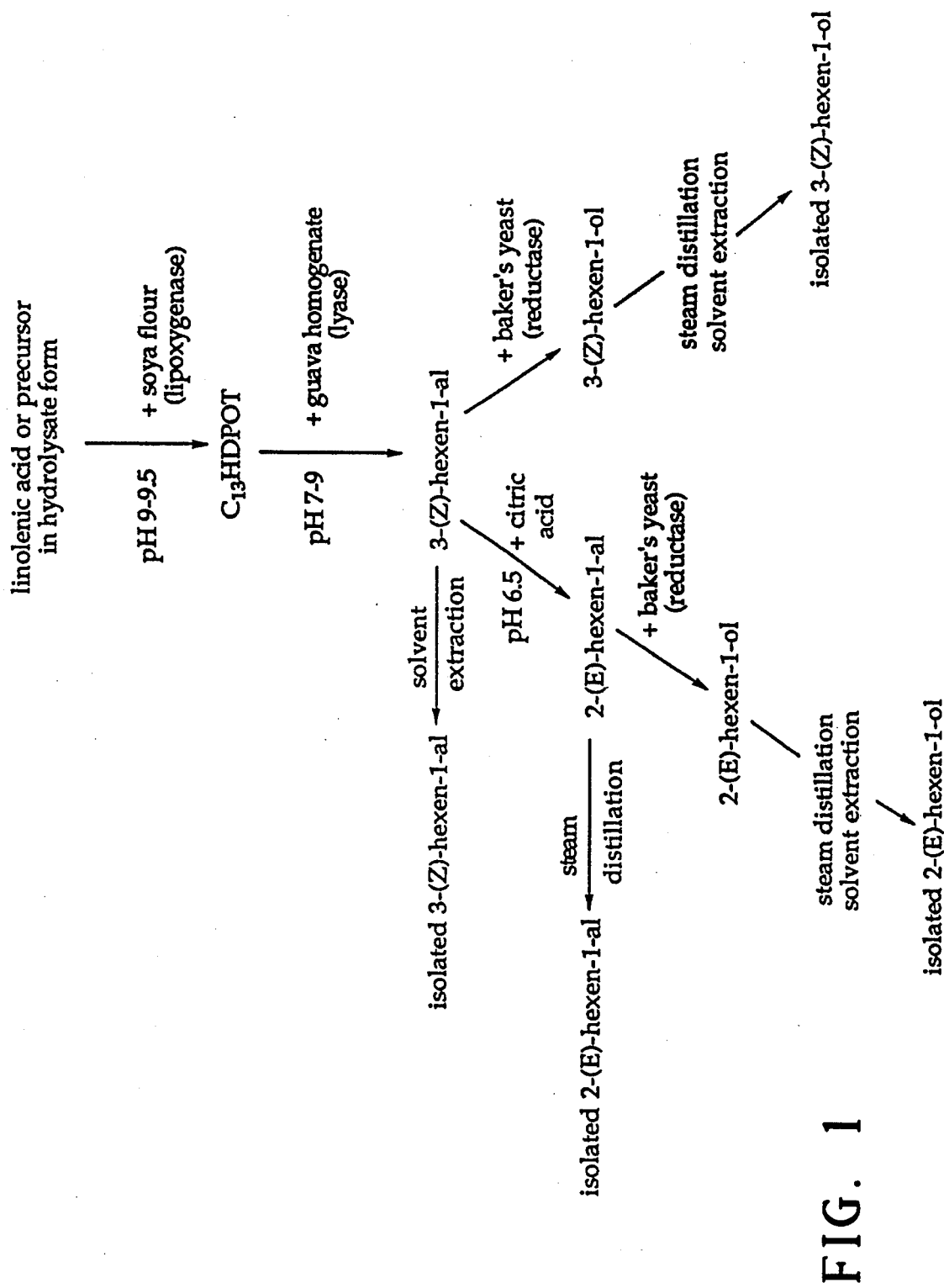
FIG. 1 is the reaction scheme for the production and isolation of 3-(Z)-hexen-1-al, 3-(Z)-hexen-1-ol, 2-(E)-hexen-1-al, and 2-(E)-hexen-1-ol from linoleic acid or precursor in hydrolysate form.

The present invention provides a method for the preparation of aldehydes and alcohols having 6 carbon atoms, which, on the one hand, satisfies the natural origin legal requirements and, on the other hand, fulfills the criteria of economic profitability.

We have, in fact, discovered that it was now possible to obtain n-hexanal, 3-(Z)-hexen-1-al and 2-(E)-hexen-1-al, as well as their corresponding alcohols, through an enzymatic process starting from linoleic or linolenic acid, or from a natural origin precursor of said acid in the form of a hydrolysate, which process comprises the following discrete reaction steps:

a) subjecting linoleic acid, respectively linolenic acid, or said precursor in hydrolysate form, to the action of a lipoxygenase in an appropriate culture medium to obtain 13-hydroperoxy-octadeca-9,11-dienoic acid ("$C_{13}$HDPO"), respectively 13-hydroperoxy-octadeca-9,11,15-trienoic acid ("$C_{13}$HDPOT");

b) converting the thus obtained "$C_{13}$HDPO", respectively "$C_{13}$HDPOT", into n-hexanal, respectively into 3-(Z)-hexen-1-al, by means of a lyase;

c) reducing the obtained n-hexanal, respectively 3-(Z)-hexen-1-al, by means of a yeast to obtain n-hexanol, respectively 3-(Z)-hexen-1-ol; or c') if necessary, isomerizing 3-(Z)-hexen-1-al under the appropriate temperature and pH conditions to obtain 2-(E)-hexen-1-al, and d) reducing the obtained 2-(E)-hexen-1-al by means of a yeast to provide 2-(E)-hexen-1-ol.

As is apparent from the preceding comments, the aldehydes are obtained by stopping the process at step b) or c'), thus before beginning their reduction by the yeast.

The desired products obtained can be separated from the reaction medium via an additional step consisting of a steam distillation followed by extraction by means of an inert organic solvent.

In the case of hexanal, the steam distillation provides two quite distinct layers of distillate, so that the hexanal can thus be separated without resorting to an extraction.

On the other hand, in the case of 3-(Z)-hexen-1-al, the best yields are obtained via extraction with an inert organic solvent, without steam distillation.

According to a preferred embodiment of the invention, the enzymatic action of the lipoxygenase is carried out by soya flour, which is added to the reaction medium under oxygen atmosphere. Thus, one obtains a hydroperoxide of linoleic acid, or 13-hydroperoxy-octadeca-9,11-dienoic acid (hereafter defined as "$C_{13}$HDPO"), respectively a hydroperoxide of linolenic acid or 13-hydroperoxy-octadeca-9,11,15-trienoic acid (hereafter defined as "$C_{13}$HDPOT"). These acids are then converted into n-hexanal, respectively into 3-(Z)-hexen-1-al, under the action of a lyase. In practice, it became apparent that it was convenient to subject "$C_{13}$HDPO", respectively "$C_{13}$HDPOT", to the action of a guava homogenate. The guava homogenate is obtained quite simply by treating the fruits in a common industrial grinding mill without prior separation of the solid matter. The conversion of the thus obtained aldehydes into the corresponding alcohols, i.e. n-hexanol and 3-(Z)-hexen-1-ol, is carried out by means of a yeast and, preferably, a yeast of the *Saccaromyces cerevisiae* type is used.

When it is desired to obtain directly the alcohol, it is suitable to subject "$C_{13}$HDPO", respectively "$C_{13}$HDPOT" to the combined action of a guava homogenate and baker's yeast.

As mentioned above, one can use as starting product linolenic acid, respectively linoleic acid, or one of their natural precursors and, to this end, we have chosen linseed oil, respectively sunflower oil. In this case, it is of course necessary to previously hydrolyze these oils, which hydrolysis can be carried out as follows.

The commercial linseed oil, respectively sunflower oil is treated at reflux with an alkaline aqueous solution, for example sodium hydroxide, in an alcohol, such as ethanol or propyleneglycol. Alternatively, the linseed oil, respectively sunflower oil, can be subjected to the enzymatic action of a lipase.

Such a treatment allows complete hydrolysis of the oil and the resulting solution is directly used in the reaction with the lipoxygenase enzymatic system to provide "$C_{13}HDPO$", respectively "$C_{13}HDPOT$". This reaction step is carried out preferably at a pH value comprised between about 9.0 and 9.5. We have observed that such a pH value was critical for obtaining the best hydroperoxide yields, a phenomenon which is probably related with the activity of the soya flour's lipoxygenase.

On the other hand, we have also observed that the temperature could play a decisive role in the proper progression of this step of the process, in the sense that a preferred temperature should lie in the vicinity of room temperature and that it is not advisable to carry out the reaction at temperatures above 30°–35° C., perhaps as a result of rearrangement of the formed hydroperoxide and of the formation of undesirable by-products.

As lipoxygenase agent, we used a soya flour which had been ground from soya beans immediately before its use. Alternatively, one could resort to a solution obtained by treating this flour with hexane, followed by mixing with a borax solution and centrifuging.

Regarding the following steps b) and c) of the process, we have also observed that obtaining the best yields was dependent on the acidity of the reaction medium, although this was not as critical as in the preceding step. In fact, the tests which led to the present invention showed that the reaction could be carried out at a pH value comprised between about 7.0 and 9.0, preferably in the vicinity of 8.0.

As indicated above, when it is desired to obtain n-hexanol or 3-(Z)-hexen-1-ol, the two steps b) and c) of lyase action, and respectively reduction, can be carried out without isolating the n-hexanal or 3-(Z)-hexen-1-al formed.

To obtain 2-(E)-hexen-1-al and 2-(E)-hexen-1-ol, one first isomerizes the 3-(Z)-hexen-1-al obtained in step b). The yield and time length of this isomerization reaction turned out to be more dependent on the temperature than on the acidity of the medium. Although the reaction can be carried out at temperatures varying between about 40° and 80° C., the best yields were obtained at temperatures of the order of 50° C. and at slightly acidic pH values, for example in the vicinity of 6.5. Such a pH can be obtained by means of citric acid.

After total isomerization of 3-(Z)-hexen-1-al into 2-(E)-hexen-1-al, the latter can be converted into 2-(E)-hexen-1-ol by means of baker's yeast.

Figure 2:
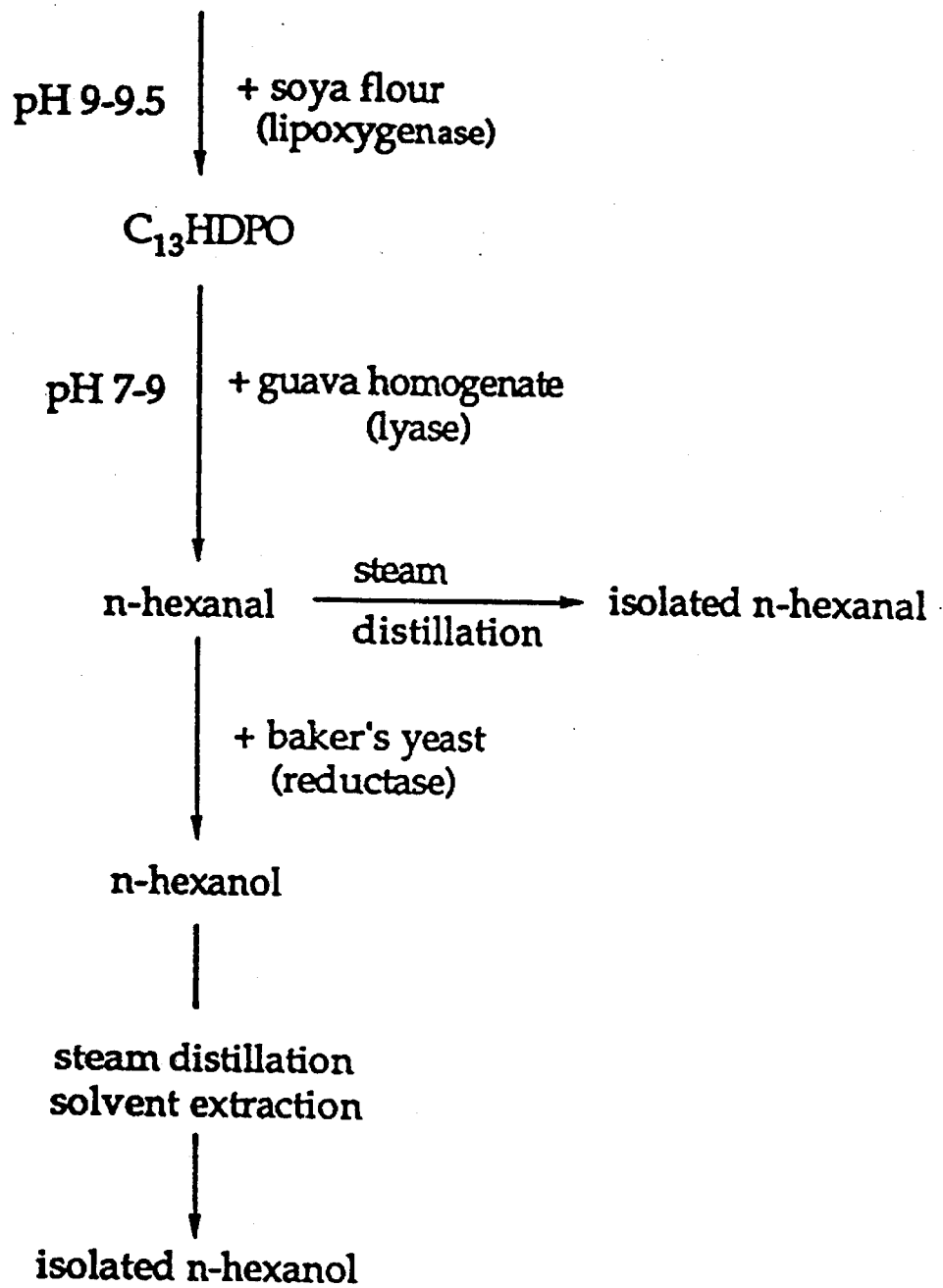
FIG. 2 is the reaction scheme for the production and isolation of n-hexanal and n-hexanol from linoleic acid or precursor in hydrolysate form.

The process of the invention can be illustrated by the scheme shown in FIG. 1 and FIG. 2.

By carrying out the process of the invention, n-hexanal was obtained in concentrations close to 5 g/kg of reaction mixture. Likewise, for n-hexanal, which represents a global yield of about 36%.

In the same way, 3-(Z)-hexen-1-ol was obtained in concentrations of the order of 4.2 g/kg of the reaction mixture, which represents a yield well above that observed when carrying out the prior art processes [0.050 g/kg].

As for 2-(E)-hexen-1-al, it was obtained in concentrations around 1.5 g/kg of reaction mixture, representing a global yield of about 20%. 2-(E)-Hexen-1-ol was obtained in yields of the order of 0.6 g/kg of reaction mixture, which represents a global yield of the order of 10%.

The invention is now described in a more detailed manner by way of the following examples wherein the temperatures are indicated in degrees centigrade and the abbreviations have the usual meaning in the art.

Modes of Carrying out the Invention

EXAMPLE 1

Preparation of n-hexanal and n-hexanol

In a 4-neck reactor equipped with a mechanical stirrer, a thermometer, an introduction funnel and a pH electrode, there were dissolved 315.3 g of a solution of sunflower oil hydrolysate in 1048 g of water and the pH value was adjusted to 9.5. The temperature of the mixture was decreased to 10°, then the mixture was degassed before introducing a flow of oxygen.

132 G of soya flour freshly ground were added to the reaction mixture while the stirring speed was increased to 1000 rpm.

After about 1 h, the oxygen absorption ceases and an iodometric titration indicates a degree of oxidation around 92%.

The resulting solution containing "$C_{13}HDPO$" was transferred into a 6 l 3-neck flask equipped with a thermometer, a stirrer and a pH electrode.

The pH value was adjusted to 8.5 and maintained at this value by addition of a 10% NaOH alkaline solution while 1400 g of guava homogenate were added. The resulting mixture was kept under stirring at 10° for 30 min, then the temperature was increased to 25°, while the evolution of the reaction was followed through periodical analysis of samples of the reaction mixture.

The n-hexanal, present at a rate of 3.80 g/kg of reaction mixture, can be separated at this stage of the process via steam distillation and separation of the organic layer followed by distillation thereof.

The process can be carried out until complete conversion of the formed n-hexanal into n-hexanol by proceeding as follows.

600 G of baker's yeast were added to the reaction mixture, followed by two other fractions of 100 g each of the same yeast added within a time period of 2½ h.

After complete disappearance of n-hexanal, distillation under vacuum was carried out [T=78°; P=460 mbar].

Thus, a fraction of 800 ml of distillate was recovered, which was extracted with 3 fractions of ether of 300 ml each. The combined organic extracts were concentrated and the obtained residue was distilled at 12 mbar to provide 13.75 g of 96% pure n-hexanol.

The table below summarizes the results obtained upon different tests carried out by varying the concentrations of guava homogenate and yeast, as well as the pH.

| | TABLEAU | | | | | | |
|---|---|---|---|---|---|---|---|
| | $C_{13}$HDPO | Guava | Baker's yeast | | | Yield in n-hexanol | |
| Ex. | /guava g/kg[2] | conc. g/kg[1] | conc. g/kg[1] | pH | Temp. °C. | g/kg[1] | Global yield % |
| 1 | 37,7 | 500 | 75 | 5 | 25 | 0,60 | 10,7 |
| 2 | 37,7 | 500 | 150 | 5 | 10 | 2,43 | 45,4 |
| 3 | 43,8 | 493 | 150 | 5 | 25 | 2,72 | 47,7 |
| 4 | 43,1 | 540 | 162 | 5 | 25 | 2,98 | 45,3 |
| 5 | 51,9 | 540 | 162 | 5 | 25 | 3,23 | 49,1 |
| 6 | 47,3 | 595 | 162 | 5 | 25 | 2,34 | 38,9 |
| 7 | 51,9 | 541 | 216 | 5 | 25 | 2,71 | 43,2 |
| 8 | 52,1 | 571 | 171 | 8,5 | 25 | 2,98 | 36,0 |
| 9 | 74,4 | 483 | 276 | 8,5 | 25 | 4,12 | 44,9 |
| 10 | 74,4 | 483 | 241 | 8,5 | 25 | 3,72 | 39,4 |
| 11 | 74,4 | 483 | 207 | 8,5 | 25 | 3,65 | 37,6 |
| 12 | 74,4 | 483 | 276 | 8,5 | 25 | 3,81 | 41,5 |

[1] ratio weight in g, by kg of reaction mixture
[2] weight ratio relative to guava weight Analogous results were obtained when replacing the sunflower oil hydrolysate by a commercial mixture of fatty acids (origin: Fluka A, Switzerland) having a content in linoleic acid of around 55%.

As lipoxygenase agent, one can also replace the powder soya flour with an homogenate obtained as follows.

The soya flour is treated successively with two fractions of hexane and then the solid part thus degreased is admixed with an identical weight of a 0.05M borax solution (5 min/4°) and the whole centrifuged (5 min/1000 rpm/5°). The solution thus freed of the solid matter was used as lipoxygenase agent.

The baker's yeast employed was a commercial yeast (origin: Hefefabrik Hindelbank, Switzerland).

EXAMPLE 2

Preparation of n-hexanal

In a 4-neck reactor equipped with a mechanical stirrer, a thermometer, an introduction funnel and a pH electrode, there were mixed 169.2 g of a commercial mixture of fatty acids having a content in linoleic acid of about 64.5%, 60 g of a 30% NaOH aqueous solution and 1048 g of water. The temperature of the mixture was adjusted to 18° and the pH to 9.5, then the mixture was degassed before introducing oxygen.

132 G of soya flour freshly ground were added to the reaction mixture while the pH was maintained at 9.5 by gradual addition of a 30% NaOH solution. The reaction proceeds as indicated in the previous example. Once the oxygen absorption ceases, the resulting solution containing 87.3 g/kg of "$C_{13}$HDPO" was transferred into another reactor and treated with a guava homogenate as described in Example 1.

The hexanal was separated from the reaction mixture by distillation at 78° and a pressure of 460 mbar. A fraction of about 280 g was thus obtained, which fraction was formed of two layers, of which the upper layer was separated and distilled at 15 mbar to provide 14.24 g of 98% pure n-hexanal, with a global yield of 35.8%.

The production of n-hexanal was thus carried out in a concentration of 5.07 g of aldehyde per kg of reaction mixture.

EXAMPLE 3

Preparation of 3-(Z)-hexen-1-ol

In a reactor equipped with a mechanical stirrer, a thermometer, an introduction funnel and a pH electrode, 197.5 g of a commercial origin mixture containing 48.2% of linolenic acid (the remainder consisting of linoleic and oleic acids), 60.5 g of 30% NaOH and 930 ml of water were stirred. The temperature was adjusted to 20° and the pH taken to 9.5.

After degassing, oxygen was introduced, then 174 g of soya flour were added to the reaction mixture, while the temperature of the mixture was maintained at 18°–22° by external cooling and the pH kept constant at 9.5 by gradual addition of a 30% NaOH solution. After about 1 h, the oxygen absorption ceases and an iodometric titration indicates a degree of oxidation around 97%. The resulting solution containing the "$C_{13}$HDPOT" was transferred into a 6 l 3-neck flask equipped with a thermometer, a stirrer and a pH electrode. The temperature of the solution was taken to 23° and the pH kept at 8.0 while 900 g of baker's yeast were added, followed, 1 min. later, by 1500 g of guava homogenate. The temperature was increased to 25° and the evolution of the reaction was followed by periodic analysis of samples of the reaction mixture. After complete vanishing of 3-(Z)-hexen-1-al, distillation under vacuum was carried out [T=78°; P=460 mbar].

A 760 g fraction was thus recovered and extracted with 3 fractions of ethyl acetate. The combined organic extracts yielded, after evaporation and distillation, 17.2 g of a raw oil which, by fractionation under 15 mbar, gave 14.36 g of 3-(Z)-hexen-1-ol, 88% pure. The global yield in hexenol was 36.9% or 3.79 g per kg of reaction mixture.

Figure 3:
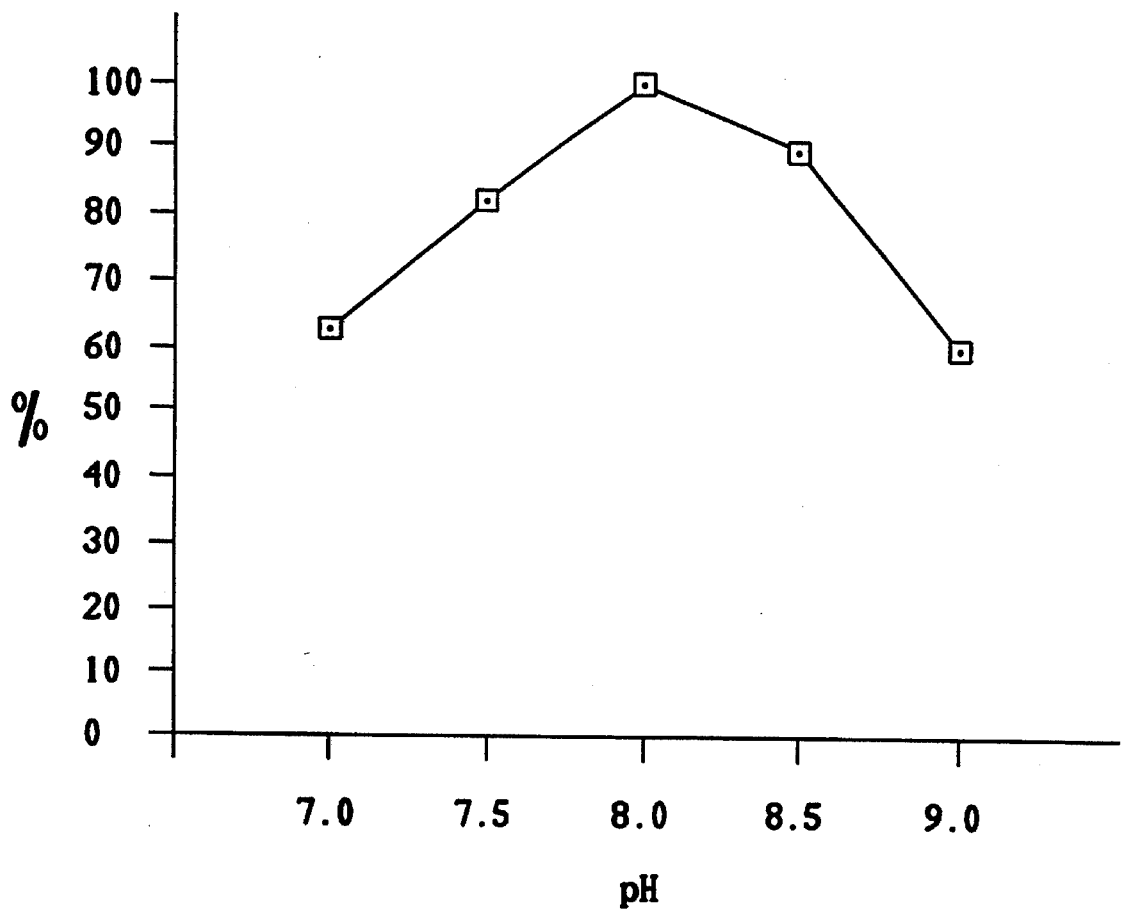
FIG. 3 is a graph of the relationship between the yield of 3-(Z)-hexen-1-ol and the pH in steps b) and c) of the present invention.

Several tests were carried out for steps b) and c) by varying the pH value. FIG. 3 summarizes the results obtained by indicating the concentration as a relative percentage of 3-(Z)-hexen-1-ol.

Following the same procedure as described above, one can convert in a similar manner hydrolyzed linseed oil instead of linolenic add. To this end, an hydrolysate obtained from a commercial linseed oil was used. The hydrolysate was prepared as follows.

103 G of raw oil were mixed with 58.0 g of a 30% NaOH aqueous solution and 80 g of ethanol, and the whole was heated to reflux under stirring.

After cooling, the solution of fatty acids thus obtained

[56.4% of linolenic acid, 16.8% of linoleic acid and 16.5% of oleic acid] solidifies into a gel.

According to a variant of the method described above, a hydrolysate of linseed oil was prepared as follows.

A mixture of 518.3 g of linseed oil, 290 g of a 30% NaOH aqueous solution and 400 g of propyleneglycol was heated to reflux during 1 h. The gel obtained after cooling is directly used in the following reaction step. The proportion of linolenic acid in the obtained mixture of fatty acids was similar to that observed in the mixture obtained following the preceding method.

As lipoxygenase agent, the powder soya flour can also be replaced by an homogenate obtained as follows.

The soya flour is treated successively with two fractions of hexane and then the solid part thus degreased is mixed with an identical weight of a 0.05M borax solution (5 min/4°) and the whole centrifuged (5 min/1000 rpm/5°). The solution thus freed of the solid parts was used as lipoxygenase agent.

The baker's yeast used was a commercial yeast [origin: Hefefabrik Hindelbank, Switzerland].

The following table summarizes the results obtained in different tests carried out by varying the concentrations of guava homogenate and yeast.

| Ex. | Starting product[1,3] | $C_{13}HDPO$ /guava g/kg | Guava conc. g/kg[2] | Baker's yeast conc. g/kg[2] | Yield in 3-(Z)-hexen-1-ol g/kg[2] | global yield[4] |
|-----|-----|------|-----|-----|------|-------|
| 1   | (a) | 71,2  | 484 | 207 | 2,25 | 25,5% |
| 2   | (b) | 69,9  | 515 | 221 | 2,58 | 31,8% |
| 3   | (b) | 87,5  | 527 | 174 | 2,84 | 25,8% |
| 4   | (b) | 87,3  | 527 | 208 | 3,36 | 33,7% |
| 5   | (b) | 97,7  | 519 | 237 | 3,79 | 36,9% |
| 6   | (b) | 99,7  | 519 | 237 | 3,68 | 36,5% |
| 7   | (b) | 99,2  | 519 | 237 | 3,57 | 34,9% |
| 8   | (b) | 96,3  | 519 | 216 | 4,20 | 41,9% |
| 9   | (b) | 98,4  | 510 | 203 | 3,72 | 35,4% |
| 10  | (b) | 73,1  | 515 | 181 | 2,49 | 31,1% |
| 11  | (b) | 73,6  | 515 | 181 | 2,47 | 29,2% |
| 12  | (b) | 101,4 | 527 | 228 | 3,66 | 32,4% |

[1](a) = linseed oil hydrolysate
(b) = mixture of fatty acids [48.2% of linolenic acid]
[2]weight in g relative to 1 kg of reaction mixture
[3]constant weight ratio of soya flour/starting product
[4]considering the purity

EXAMPLE 4

Preparation of 2-(E)-hexen-1-al

In a 5-neck reactor equipped with a mechanical stirrer, a thermometer, an introduction funnel and a pH electrode, there were dissolved 315.3 g of a solution of linseed oil hydrolysate in 1248 g of water and the mixture stirred at 20°. The pH value was adjusted to 9.5 and the mixture was degassed before introducing a flow of oxygen.

132 G of soya flour freshly ground were added to the reaction mixture while the stirring speed was increased to 1000 rpm. The temperature was kept between 18° and 22° by means of a cold water bath.

After about 1 h, the oxygen absorption ceases and an iodometric titration indicates an oxidation degree of about 95%.

The resulting solution containing the "$C_{13}HDPOT$" was transferred into a 6 l 3-neck flask equipped with a thermometer, a stirrer and a pH electrode.

The temperature was adjusted to 5° and 2 kg of guava homogenate, cooled to 5°, were added thereto under vigorous stirring. The resulting mixture was kept under stirring at this temperature for 15 min, the pH measuring 7.3. 5 G of citric acid were added all at once and the pH decreased to 6.5.

The electrode was then replaced by a distillation bridge and the mixture distilled at 78° (P=460 mbar).

A fraction of 700 g (about 20% of the total reaction volume) were condensed and extracted with 3 fractions of ether, of 150 ml each. The combined organic extracts were dried over $Na_2SO_4$ and concentrated. The obtained residue (7.4 g) was distilled at 30 mbar to yield a fraction of 6.72 g of 79% pure 2-(E)-hexen-1-al.

EXAMPLE 5

Preparation of 2-(E)-hexen-1-ol

In a 5-neck reactor equipped with a mechanical stirrer, a thermometer, an introduction funnel and a pH electrode, there were mixed 134.9 g of a commercial mixture of fatty acids, having a content in linolenic acid of about 48.2%, 41 g of a 30% NaOH aqueous solution and 1248 g of water. The temperature of the mixture was adjusted to 20° and the pH to 9.5, then the mixture was degassed before introducing oxygen.

135 G of soya flour freshly ground were added to the reaction mixture while the pH was kept at 9.5 by gradual addition of a 30% NaOH solution. The reaction proceeds as indicated in the preceding example. Once the oxygen absorption had ceased, the obtained solution containing the "$C_{13}HDPOT$" was transferred into another reactor and treated with a guava homogenate as described in Example 1.

5 G of citric acid were added and the mixture was heated to 50°, the isomerization of 3-(Z)-hexen-1-al into 2-(E)-hexen-1-al being followed by GC. After 90 min, the conversion was completed and the temperature of the reaction was lowered to 25°.

500 G of baker's yeast were added and the reaction followed by sampling every 30 min for analysis. After 60 min, 85% of the aldehyde had been converted into alcohol.

The electrode was replaced by a distillation bridge and the mixture distilled at 78° (P=460 mbar).

A fraction of 800 g was condensed and extracted as described in Example 1. Distillation of the residue under 30 mbar pressure yielded 3.76 g of 63% pure 2-(E)-hexen-1-ol.

What is claimed is:

1. An enzymatic process for the preparation of n-hexanal, 3-(Z)-hexen-1-al, 2-(E)-hexen-1-al, or their corresponding alcohols, starting from linoleic or linolenic acid, or from a natural origin precursor thereof consisting of a hydrolyzed oil, said process comprising the following discrete reaction steps:

a) adding to said acid or natural precursor thereof soya flour in a pure oxygen atmosphere and in a reaction medium, which soya flour contains lipoxygenase to convert said acid, to form 13-hydroperoxy-octadeca-9,11-dienoic acid or 13-hydroperoxy-octadeca- 9,11,15-trienoic acid;

b) adding a guava homogenate to the medium, which homogenate contains lyase to convert the 13-hydroperoxy-octadeca-9,11-dienoic acid into n-hexanal or the 13-hydroperoxy-octadeca-9,11,15-trienoic acid into 3-(Z)-hexen-1-al; and either c) recovering the formed n-hexanal or 3-(Z)-hexen-1-al from the medium; or c') adding a yeast to the medium to reduce n-hexanal into n-hexanol or 3-(Z)-hexen-1-al into 3-(Z)-hexen-1-ol; and recovering the formed n-hexanol or 3-(Z)-hexen-1-ol from the medium; or c") isomerizing said 3-(Z)-hexen-1-al under temperature and pH conditions effective to obtain 2-(E)-hexen-1-al, and either recovering the formed 2-(E)-hexen-1-al from the medium or adding a yeast to said 2-(E)-hexen-1-al to form 2-(E)-hexen-1-ol and recovering the latter from the medium.

2. The process of claim 1, wherein the formed 2-(E)-hexen-1-al is recovered by steam distillation followed by extraction with an inert organic solvent.

3. The process of claim 1, wherein the n-hexanal is recovered by steam distillation followed by a separation of an organic layer of the distillate.

4. The process of claim 1, wherein the 3-(Z)-hexen-1-al is recovered through extraction with an inert organic solvent.

5. The process of claim 1, wherein the n-hexanol, 3-(Z)-hexen-1-ol or 2-(E)-hexen-1-ol is recovered by steam distillation followed by extraction with an inert organic solvent.

6. The process of claim 1, wherein the pH of the reaction medium during step a) is maintained at between about 9 and 9.5.

7. The process of claim 1, wherein the yeast in step c') or c") is *Saccharomyces cerevisiae*.

8. The process of claim 1, wherein a guava homogenate and *Saccharomyces cerevisiae* are added in combination to the 13-hydroperoxy-octadeca- 9,11-dienoic acid to form n-hexanol or to the 13-hydroperoxy-octadeca-9,11,15-trienoic acid to form 3-(Z)-hexen-1-ol.

9. The process of claim 1, wherein step c") is carried out at a temperature of about 50° C. and at a pH of about 6.5.

10. The process of claim 1, wherein step b) is carried out at a pH of between about 7 and 9.

11. The process of claim 1, wherein the reaction medium is of water.

12. An enzymatic process for the preparation of n-hexanal, 3-(Z)-hexen-1-al, 2-(E)-hexen-1-al, or their corresponding alcohols, starting from linoleic or linolenic acid, or from a natural origin precursor thereof consisting of a hydrolyzed oil, said process comprising the following reaction steps:

(a) adding to said acid or natural precursor thereof soya flour, in pure oxygen atmosphere and in a reaction medium of water, the pH of which is maintained between 9 and 9.5, which soya flour contains lipoxygenase to convert said acid to 13-hydroperoxy-octadeca-9,11-dienoic acid or 13-hydroperoxy-octadeca-9,11,15-trienoic acid;

(b) adding a guava homogenate to the medium, which homogenate contains lyase to convert the 13-hydroperoxy-octadeca- 9,11-dienoic acid to n-hexanal or the 13-hydroperoxy-octadeca- 9,11,15-trienoic acid to 3-(Z)-hexen-1-al; and either c) recovering the formed n-hexanal or 3-(Z)-hexen-1-al from the medium; or c') adding a yeast to the medium to reduce n-hexanal into n-hexanol or 3-(Z)-hexen-1-al into 3-(Z)-hexen-1-ol; and recovering the formed n-hexanol or 3-(Z)-hexen-1-ol from the medium; or c") isomerizing said 3-(Z)-hexen-1-al under temperature and pH conditions effective to obtain 2-(E)-hexen-1-al, and either recovering the formed 2-(E)-hexen-1-al from the medium or adding a yeast to said 2-(E)-hexen-1-al to form 2-(E)-hexen-1-ol and recovering the latter from the medium.

13. The process of claim 12, wherein step b) is carried out at a pH value of between about 7 and 9.

14. The process of claim 12, wherein the yeast is *Saccharomyces cerevisiae*.

15. An enzymatic process for the preparation of n-hexanal, 3-(Z)-hexen-1-al, 2-(E)-hexen-1-al, or their corresponding alcohols, starting from linoleic or linolenic acid, or from a natural origin precursor thereof consisting of a hydrolyzed oil, said process comprising the following reaction steps:

(a) adding to said acid or natural precursor thereof soya flour, in pure oxygen atmosphere and in a reaction medium of water, the pH of which is maintained between 9 and 9.5, which soya flour contains lipoxygenase to convert said acid to 13-hydroperoxy-octadeca-9,11-dienoic acid or 13-hydroperoxy-octadeca-9,11,15-trienoic acid;

(b) adjusting the pH value of the medium to a value of between about 7 and 9 and adding to the medium a guava homogenate containing lyase to convert the 13-hydroperoxy-octadeca- 9,11-dienoic acid to n-hexanal or the 13-hydroperoxy-octadeca- 9,11,15-trienoic acid to 3-(Z)-hexen-1-al; and either c) recovering the formed n-hexanal or 3-(Z)-hexen-1-al from the medium; or c') adding *Saccharomyces cerevisiae* to the medium to reduce n-hexanal into n-hexanol or 3-(Z)-hexen-1-al into 3-(Z)-hexen-1-ol; and recovering the formed n-hexanol or 3-(Z)-hexen-1-ol from the medium; or c") isomerizing said 3-(Z)-hexen-1-al under temperature and pH conditions effective to obtain 2-(E)-hexen-1-al, and either recovering the formed 2-(E)-hexen-1-al from the medium or adding *Saccharomyces cerevisiae* to said 2-(E)-hexen-1-al to form 2-(E)-hexen-1-ol and recovering the latter from the medium.

* * * * *